United States Patent [19]

Benner

[11] Patent Number: 5,432,272
[45] Date of Patent: Jul. 11, 1995

[54] METHOD FOR INCORPORATING INTO A DNA OR RNA OLIGONUCLEOTIDE USING NUCLEOTIDES BEARING HETEROCYCLIC BASES

[76] Inventor: Steven A. Benner, Hadlaubstrasse 151, CH-8006 Zurich, Switzerland

[21] Appl. No.: 594,290

[22] Filed: Oct. 9, 1990

[51] Int. Cl.⁶ .................... C07H 23/00; C12P 19/34
[52] U.S. Cl. .................... 536/25.3; 536/25.33; 435/91.1; 435/91.51; 435/9.41
[58] Field of Search .................... 536/25, 23, 24, 26, 536/27, 29, 28, 25.3, 25.33; 435/91, 91.1, 91.51, 91.41

[56] References Cited

U.S. PATENT DOCUMENTS 4,959,463  9/1990  Froehler et al. .................... 536/27
5,047,519  9/1991  Hobbs, Jr. et al. .................... 536/23

OTHER PUBLICATIONS

Langer et al. (1981) PNAS vol. 78, pp. 6633–6637.
Cech et al. (1986) Ann. Rev. Biochem. vol. 55, p. 599.
Szostak (1986) Nature 332, 83.
Been et al. (1988) Science 239, 1412.
Leary et al. (1983) PNAS 80, 4045.
Chen et al. (1988) Biochem 27, 6032.
Haseloff et al. (1988) Nature 334, 585.
Sarver et al. (1990) Science 247, 1222–1225.
Noren et al. (1989) Science 244, 182.
Bain et al. (1989) J. Am. Chem. Soc. 111, 8013–8014.
Rich (1962) Horizons in Biochemistry, Kasha et al. editors, N.Y., Academic Press, 103–126.
Saenger (1985) Nucleic Acid Chemistry, Springer—Verlag.
Zubay (1988) The Roots of Modern Biochemistry, Kleinkauf et al. Berlin, Walter de Grumpton & Co., 911–916.
Switzer et al. (1989) J. Am. Chem. Soc. 111, 8322.
Piscisilli et al. (1990) Nature 343, 33–37.
Uhlenbeck (1987), Nature 328, 18.
Chu et al. (1977) J. Org. Chem. 42, 711.
Ugarkar et al. (1984) Heterocyl. Chem. 21, 1865–1870.
Milligan et al. (1987) Nucleic Acids Res. 15, 8783.
Coleman et al. (1988) Biochemistry, 27, 3966.
Roy et al. (1983), Nucleosides and Nuclestides, 2, 237.
Cobianchi et al. (1987) Meth. Enzymol. 152, 94.
Bartholomew et al. (1975) J. Org. Chem. 40, 3708–3713.
Kimura et al. (1980) Bull. Soc. Chem. Jap. 53, 3670.
Mantsch et al. (1975) Biochemistry 14, 5593.
Sgaramella et al. (1972), J. Mol. Biol., 72, 427.
Sanger et al. (1975), J. Mol. Biol., 94, 441.

Primary Examiner—Stephen G. Walsh
Assistant Examiner—Gian P. Wang

[57] ABSTRACT

The disclosure describes a method for incorporating into double stranded DNA and RNA base pairs composed of pairing units that fit the Watson-Crick geometry in that they involve a monocyclic six membered ring pairing with a fused bicyclic heterocyclic ring system composed of a five member ring fused with a six membered ring, with the orientation of the heterocycles with respect to each other and with respect to the backbone chain analogous to that found in DNA and RNA, but with a pattern of hydrogen bonds holding the base pair together different from that found in the AT and GC base pairs (a "non-standard base pair").

7 Claims, 5 Drawing Sheets

Generalized structures for 4 non-standard base pairs formed between 8 non-standard bases

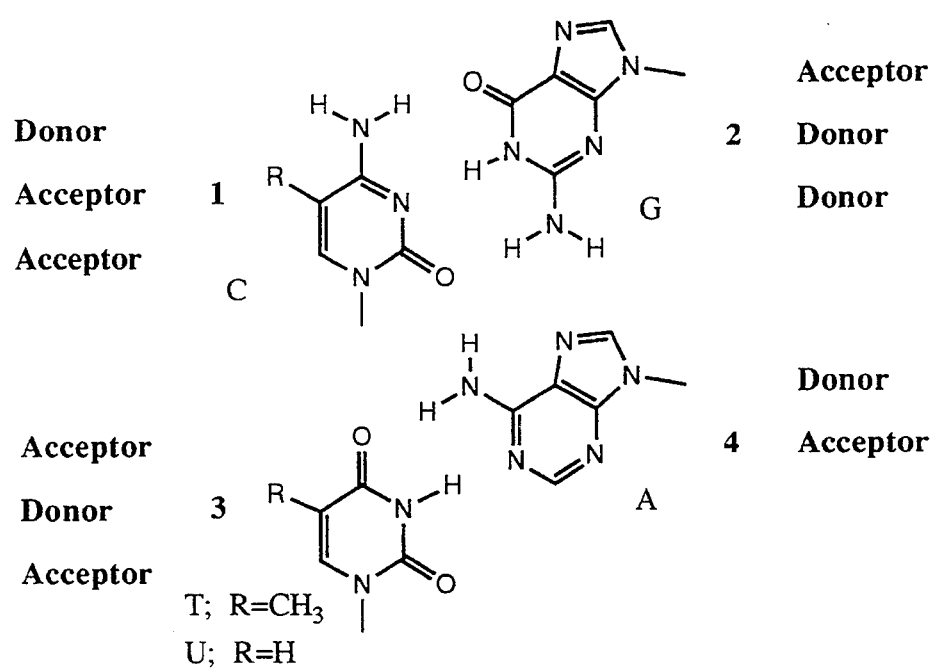
Figure 1: The two natural base pairs formed between the four natural bases

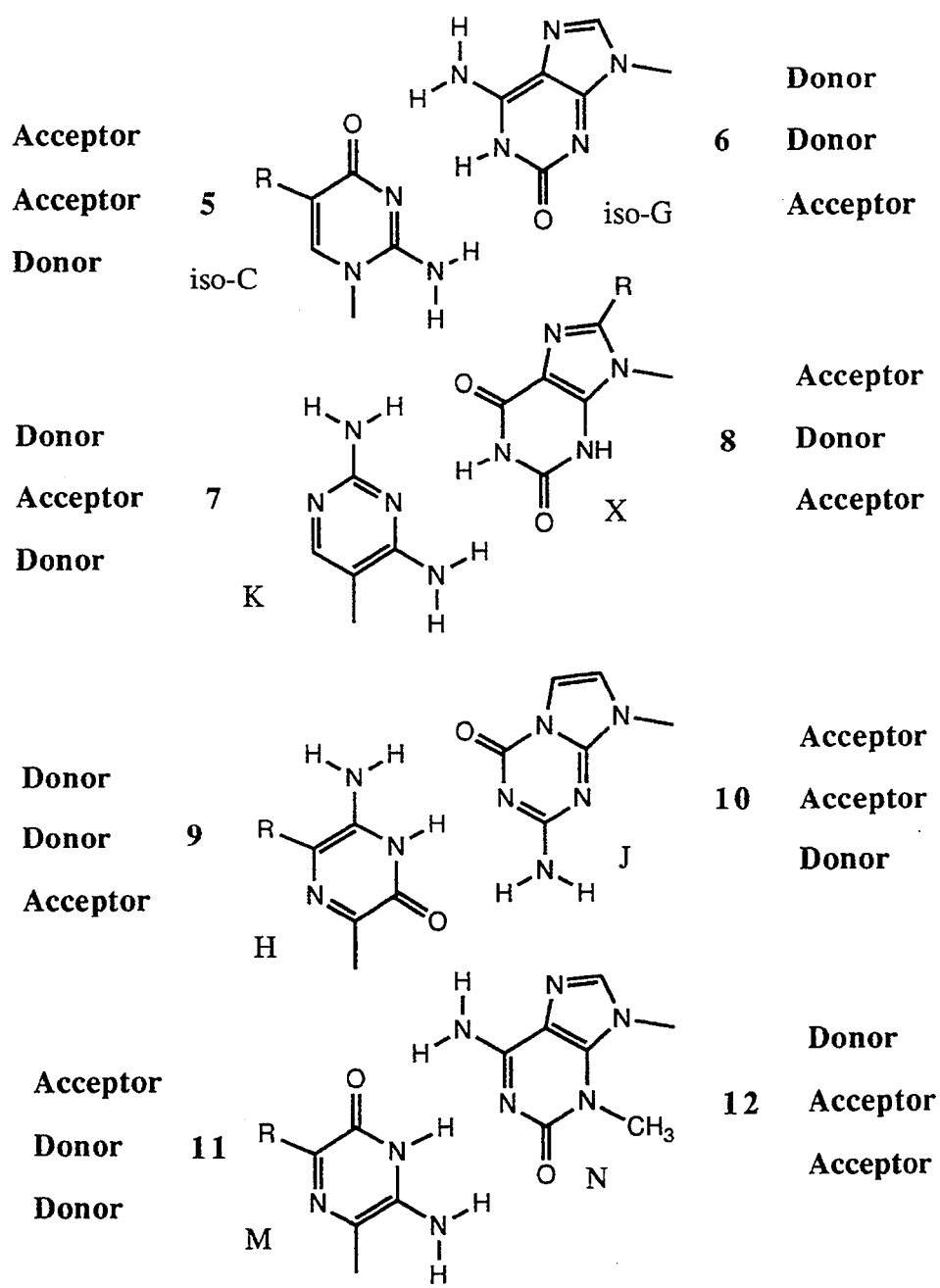
Figure 2: Examples of 4 non-standard base pairs formed between 8 non-standard bases Figure 3: Novel base pair discussed by Zubay
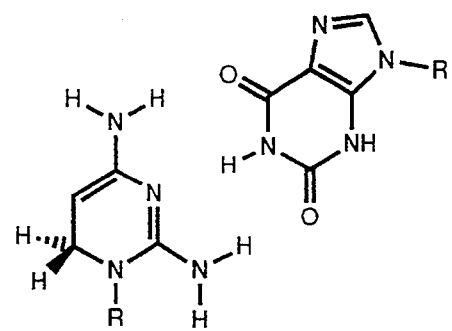

Figure 4: Generalized structures for 4 non-standard base pairs formed between 8 non-standard bases
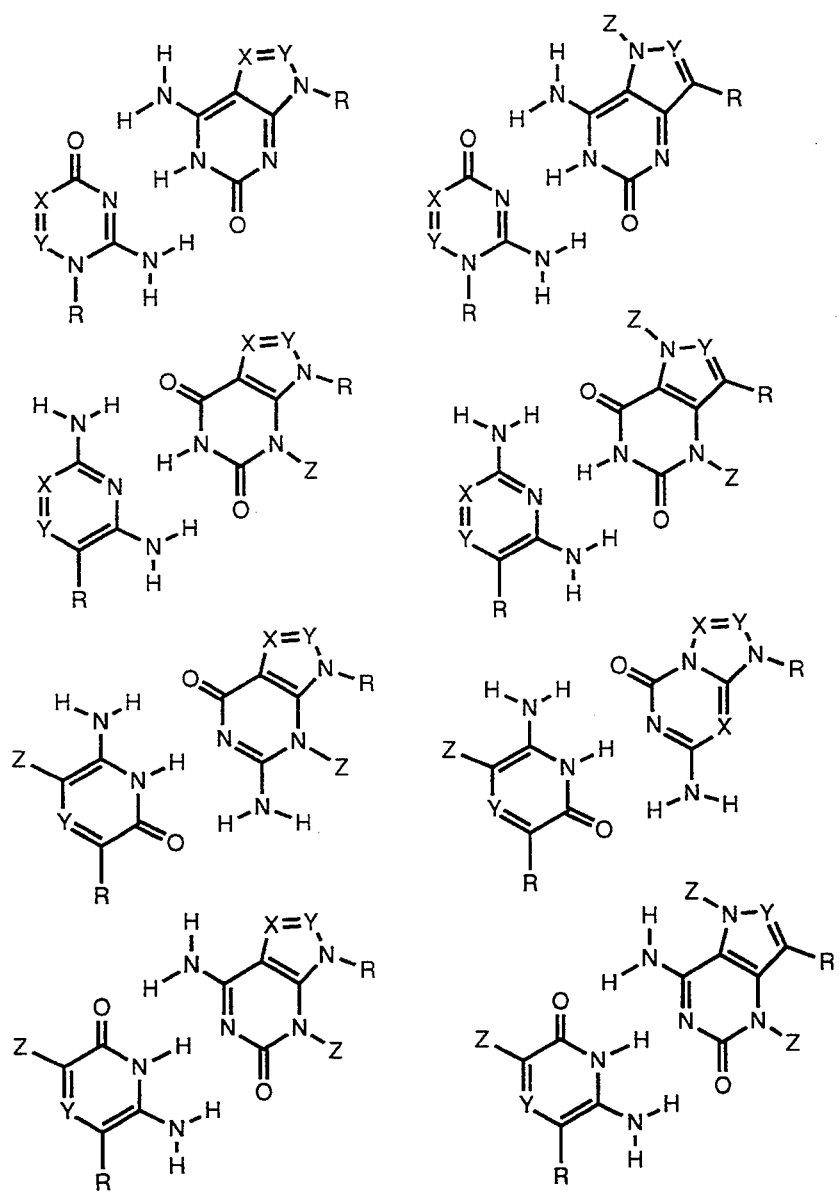

Figure 5: Templates used in the Examples

Templates for T7 RNA polymerase d-5'-GATTTTGA
d-3'-CTAAAACTGGKGA d-5'-GATTTTGA
d-3'-CTAAAACTGG*iso*-CGA d-5'-GATTTTGA
d-3'-CTAAAACTGGTGA d-5'-GATTTTGA
d-3'-CTAAAACTGGCGA Templates for DNA polymerase d-5'-TAATACGACTCACTATAG
d-3'-ATTATGCTGAGTGATATCGCGGCKCGA d-5'-TAATACGACTCACTATAG
d-3'-ATTATGCTGAGTGATATCGCGGC*iso*-CCGA d-5'-TAATACGACTCACTATAG
d-3'-ATTATGCTGAGTGATATCGCGGCCCGA

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 13
        ( B ) TYPE: nucleic acid
        ( C ) STRANDEDNESS: single
        ( D ) TOPOLOGY: linear ( i i ) MOLECULE TYPE:
        ( A ) DESCRIPTION: nucleic acid ( v i ) ORIGINAL SOURCE: synthetic ( x ) PUBLICATION INFORMATION:
        ( A ) AUTHORS:
            Switzer, C. Y.
            Moroney , S. E.
            Benner, S. A.
        ( B ) TITLE: Enzymatic Incorporation of a New Base Pair into DNA and RNA
        ( C ) JOURNAL: Journal of the American Chemical Society
        ( D ) VOLUME: 111
        ( F ) PAGES: 8322-8323
        ( G ) DATE: 1989

( x i ) SEQUENCE DESCRIPTION: SEQ ID NO:1:

A G T G G T C A A A  A T C  1 3

( 2 ) INFORMATION FOR SEQ ID NO:2:

( i ) SEQUENCE CHARACTERISTICS:
        ( A ) LENGTH: 13
        ( B ) TYPE: nucleic acid
        ( C ) STRANDEDNESS: single
        ( D ) TOPOLOGY: linear ( i i ) MOLECULE TYPE:
        ( A ) DESCRIPTION: nucleic acid ( v i ) ORIGINAL SOURCE: synthetic ( x ) PUBLICATION INFORMATION:
        ( A ) AUTHORS:
            Switzer, C. Y.
            Moroney , S. E.
            Benner, S. A.

-continued (B) TITLE: Enzymatic Incorporation of a New Base Pair into
      DNA and RNA
  (C) JOURNAL: Journal of the American Chemical Society
  (D) VOLUME: 111
  (F) PAGES: 8322-8323
  (G) DATE: 1989

(xi) SEQUENCE DESCRIPTION: SEQ ID NO:2:

AGCGGTCAAA ATC 13

(2) INFORMATION FOR SEQ ID NO:3:

(i) SEQUENCE CHARACTERISTICS:
      (A) LENGTH: 18
      (B) TYPE: nucleic acid
      (C) STRANDEDNESS: single
      (D) TOPOLOGY: linear (ii) MOLECULE TYPE:
      (A) DESCRIPTION: nucleic acid (vi) ORIGINAL SOURCE: synthetic (x) PUBLICATION INFORMATION:
      (A) AUTHORS:
          Switzer, C. Y.
          Moroney, S. E.
          Benner, S. A.
      (B) TITLE: Enzymatic Incorporation of a New Base Pair into
          DNA and RNA
      (C) JOURNAL: Journal of the American Chemical Society
      (D) VOLUME: 111
      (F) PAGES: 8322-8323
      (G) DATE: 1989

(xi) SEQUENCE DESCRIPTION: SEQ ID NO:3:

TAATACGACT CACTATAG 18

(2) INFORMATION FOR SEQ ID NO:4:

(i) SEQUENCE CHARACTERISTICS:
      (A) LENGTH: 18
      (B) TYPE: nucleic acid
      (C) STRANDEDNESS: single
      (D) TOPOLOGY: linear (ii) MOLECULE TYPE:
      (A) DESCRIPTION: nucleic acid (vi) ORIGINAL SOURCE: synthetic (x) PUBLICATION INFORMATION:
      (A) AUTHORS:
          Switzer, C. Y.
          Moroney, S. E.
          Benner, S. A.
      (B) TITLE: Enzymatic Incorporation of a New Base Pair into
          DNA and RNA
      (C) JOURNAL: Journal of the American Chemical Society
      (D) VOLUME: 111
      (F) PAGES: 8322-8323
      (G) DATE: 1989

(xi) SEQUENCE DESCRIPTION: SEQ ID NO:4:

TAATACGACT CACTATAG 18

(2) INFORMATION FOR SEQ ID NO:5:

(i) SEQUENCE CHARACTERISTICS:
      (A) LENGTH: 18
      (B) TYPE: nucleic acid
      (C) STRANDEDNESS: single
      (D) TOPOLOGY: linear (ii) MOLECULE TYPE:
      (A) DESCRIPTION: nucleic acid (vi) ORIGINAL SOURCE: synthetic (x) PUBLICATION INFORMATION:
    (A) AUTHORS:
        Piccirilli, J. A.
        Krauch, T.
        Moroney, S. E.
        Benner, S. A.
    (B) TITLE: Extending the Genetic Alphabet: Enzymatic Incorporation of a New Base Pair into DNA and RNA
    (C) JOURNAL: Nature
    (D) VOLUME: 343
    (F) PAGES: 33-37
    (G) DATE: 1990

(xi) SEQUENCE DESCRIPTION: SEQ ID NO:5:

TAATACGACT CACTATAG 18

(2) INFORMATION FOR SEQ ID NO:6:

(i) SEQUENCE CHARACTERISTICS:
        (A) LENGTH: 27
        (B) TYPE: nucleic acid
        (C) STRANDEDNESS: single
        (D) TOPOLOGY: linear (ii) MOLECULE TYPE:
        (A) DESCRIPTION: nucleic acid (vi) ORIGINAL SOURCE: synthetic (x) PUBLICATION INFORMATION:
        (A) AUTHORS:
            Switzer, C. Y.
            Moroney, S. E.
            Benner, S. A.
        (B) TITLE: Enzymatic Incorporation of a New Base Pair into DNA and RNA
        (C) JOURNAL: Journal of the American Chemical Society
        (D) VOLUME: 111
        (F) PAGES: 8322-8323
        (G) DATE: 1989

(xi) SEQUENCE DESCRIPTION: SEQ ID NO:6:

AGCCCGGCGC TATAGTGAGT CGTATTA 27

METHOD FOR INCORPORATING INTO A DNA OR RNA OLIGONUCLEOTIDE USING NUCLEOTIDES BEARING HETEROCYCLIC BASES

BACKGROUND OF THE INVENTION

FIELD OF THE INVENTION

This invention pertains to increasing the number of building blocks that can be incorporated independently into oligonucleotides via DNA and RNA polymerases, and nucleoside analogs capable of forming non-standard Watson-Crick base pairs joined by patterns of hydrogen bonding different from those found in the adenine-thymine and cytosine-guanine base pairs.

SUMMARY OF THE INVENTION

The objective of this invention is to increase the number of independently replicatable building blocks that can be incorporated into DNA and RNA via template directed polymerization. The objective is accomplished by a method for incorporating into double stranded DNA and RNA base pairs composed of pairing units that fit the Watson-Crick geometry in that they involve a monocyclic six membered ring pairing with a fused bicyclic heterocyclic ring system composed of a five member ring fused with a six membered ring, with the orientation of the heterocycles with respect to each other and with respect to the backbone chain analogous to that found in DNA and RNA, but with a pattern of hydrogen bonds holding the base pair together different from that found in the AT and GC base pairs (a "non-standard base pair").

BRIEF DESCRIPTION OF FIGURES

FIG. 1: The two natural base pairs formed between the four natural bases
FIG. 2: General structure of four novel base pairs formed between eight novel bases disclosed here
FIG. 3: Novel base pair discussed by Zubay
FIG. 4: Generalized structures
FIG. 5: Templates used in the examples

DESCRIPTION OF THE PREFERRED EMBODIMENTS

Natural oligonucleotides bind to complementary oligonucleotides according to the well-known rules of base pairing first elaborated by Watson and Crick, where adenine (A) pairs with thymine (T) or uracil (U), and guanine (G) pairs with cytosine (C), with the complementary strands anti-parallel to one another. These pairing rules allow for the specific hybridization of an oligonucleotide with complementary oligonucleotides, making oligonucleotides valuable as probes in the laboratory, in diagnostic applications, as messages that can direct the synthesis of specific proteins, and in a wide range of other applications well known in the art. Further, the pairing is the basis by which enzymes are able to catalyze the synthesis of new oligonucleotides that are complementary to template nucleotides. In this synthesis, building blocks (normally the triphosphates of ribo or deoxyribo derivatives of A, T, U, C, or G) are directed by a template oligonucleotide to form a complementary oligonucleotide with the correct sequence. This process is the bases for replication of all forms of life, and also serves as the basis for all technologies for enzymatic synthesis and amplification of specific heterosequence nucleic acids by enzymes such as DNA and RNA polymerase, and in the polymerase chain reaction.

The Watson-Crick pairing rules can be understood chemically in terms of the arrangement of hydrogen bonding groups on the heterocyclic bases of the oligonucleotide, groups that can either be hydrogen bond donors or acceptors (FIG. 1). In the standard Watson-Crick geometry, a large purine base pairs with a small pyrimidine base; thus, the AT base pair is the same size as a GC base pair. This means that the rungs of the DNA ladder, formed from either AT or GC base pairs, all have the same length.

Further recognition between bases is determined by hydrogen bonds between the bases. Hydrogen bond donors are heteroatoms (nitrogen or oxygen in the natural bases) bearing a hydrogen; hydrogen bond acceptors are heteroatoms (nitrogen or oxygen in the natural bases) with a lone pair of electrons. In the geometry of the Watson-Crick base pair, a six membered ring (in natural oligonucleotides, a pyrimidine) is juxtaposed to a ring system composed of a fused six membered ring and a five membered ring (in natural oligonucleotides, a purine), with a middle hydrogen bond linking two ring atoms, and hydrogen bonds on either side joining functional groups appended to each of the rings, with donor groups paired with acceptor groups (FIG. 1).

Derivatized oligonucleotide building blocks, where a side chain has been appended to one of the nucleoside bases A, T, U, G, or C (the "normal" bases), have application because of their combination of Watson-Crick base pairing and special reactivity associated with the chemical properties of the side chain. For example, oligonucleotides containing a T to which is appended a side chain bearing a biotin residue can first bind to a complementary oligonucleotide, and the hybrid can then be isolated by virtue of the specific affinity of biotin to avidin (Langer, P. R.; Waldrop, A. A.; Ward, D. C. (1981) Proc. Nat. Acad. Sci. 78, 6633–6637), and finds application in diagnostic work. Oligonucleotides containing special functional groups (e.g., thiols or hydrazines) can be immobilized to solid supports more readily than those composed solely of the five "natural" bases.

Often, derivatized building blocks can be incorporated into oligonucleotides by enzymatic transcription of natural oligonucleotide templates in the presence of the triphosphate of the derivatized nucleoside, the substrate of the appropriate (DNA or RNA) polymerase. In this process, a natural nucleoside is placed in the template, and standard Watson-Crick base pairing is exploited to direct the incoming modified nucleoside opposite to it in the growing oligonucleotide chain.

However, the presently available base pairs are limited in that there are only two mutually exclusive hydrogen bonding patterns available in natural DNA. This means that should one wish to introduce a modified nucleoside based on one of the natural nucleosides into an oligonucleotide, it would be incorporated wherever the complementary natural nucleoside is found in the template. For many applications, this is undesirable.

Many of the limitations that arise from the existence of only four natural nucleoside bases, joined in only two types of base pairs via only two types of hydrogen bonding schemes, could be overcome were additional bases available that could be incorporated into oligonucleotides, where the additional bases presented patterns of hydrogen bond donating and accepting groups in a pattern different from those presented by the natural bases, and therefore could form base pairs exclusively with additional complementary bases. The purpose of this invention is to describe compositions of matter containing these additional bases, and methods for their incorporation into analogs of oligonucleotides.

In the naturally-occurring base pairs, the pyrimidines components present an acceptor-donor-acceptor (T) or a donor-acceptor-acceptor (C) pattern of hydrogen bonds to a purine on an opposite strand. This invention is based on the fact that bases with other patterns of hydrogen bond donating and accepting groups can fit the standard Watson-Crick geometry. For example, FIG. 2 discloses four base pairs that have still different patterns, an acceptor-acceptor-donor pattern for iso-C, and donor-acceptor-donor pattern for K. Bases, pairing schemes, and base pairs that have hydrogen bonding patterns different from those found in the AT and GC base pairs are here termed "non-standard". Although not found (so far) in Nature, the non-standard base pairs shown in FIG. 2) apparently can fit into the DNA ladder in a standard Watson-Crick duplex.

Further, the patterns of hydrogen bonds in these non-standard pyrimidines are different from each other, and different from those in the natural pyrimidines T and C. This suggested that in an enzyme-catalyzed polymerization, it might be possible for each non-standard pyrimidine to recognize uniquely its complementary purine with high fidelity. Thus, it should be possible to make copies of a DNA molecule containing all 12 bases simply by following an expanded set of Watson-Crick rules: A pairs with T, G pairs with C, iso-C pairs with iso-G, and K pairs with X, H pairs with J, and M pairs with N (FIG. 2). In other words, it should be possible to have a genetic alphabet with twelve bases instead of four.

Statements considering non-standard base pairs in a general way can, to our knowledge, be found only three times previously in the literature. Considering possible bases that might have been incorporated into nucleic acids in the first forms of life on the earth two to four billion years ago, Rich mentions the base pair between iso-G and iso-G (Rich, A. (1962), Horizons in Biochemistry, Kasha, M. and Pullman, B. editors, N.Y., Academic Press, 103–126) as a base pair that was conceivable, but rejected, by the earliest forms of life. However, Rich did not disclose nor make obvious the process disclosed here employing contemporary DNA and RNA polymerases as part of a process for incorporating the base pair between iso-G and iso-G into oligonucleotides. Saenger (Saenger, W. (1988) *Principles of Nucleic Acid Structure* New York, Springer-Verlag, pages 114–115) also mentions this base pair, but concludes, based on the fact that iso-G has a alternate tautomeric forms (vide infra), that it has no utility as part of an oligonucleotide that is to be copied.

Zubay (Zubay, G. (1988) *The Roots of Modern Biochemistry*, Kleinkauf, von Doehren, Jaenicke, Berlin, Walter de Gruyter & Co. 911-916) suggested that 2,4-diamino-5,6-dihydropyryimidine-1-riboside, with a donor-acceptor-donor pattern, might be able to pair with xanthosine (FIG. 3). In Zubay's suggested pyrimidine, however, the pyrimidine ring is not aromatic and therefore not planar. Although it has never been examined experimentally, we believe on these grounds that it would not participate well in "base stacking," the interaction (vide supra) that is important for the stability of a double helix. Further, Zubay's base incorporates the structural unit known as a "vinylogous enamine", a structural unit that is likely to be unstable in acidic solution. Thus, we doubt that it can be incorporated into an oligonucleotide by enzymatic transcription of a complementary oligonucleotide.

Zubay discloses neither experimental studies with his suggested base nor the potential utility of a new base pair that would arise were the new base a substrate for DNA and RNA polymerases present in the modern world. Further, the possibility of constructing additional base pairing schemes (such as the non-standard base pairs disclosed in FIG. 2) was explicitly denied. Zubay writes "We have searched for other purine-pyrimidine base pairs with different arrangements of hydrogen bonding groups that would satisfy the criterion of exclusive pairing. No additional pairs have been found. Thus except for modifications at non-hydrogen bonding sites the additional base pair described here may be unique. "This comment from a prominent figure in American biochemistry supports the notion that the invention disclosed here, where DNA and RNA polymerases can be used in a method to incorporate non-standard base pairs into oligonucleotides, is not obvious to one skilled in the art.

Should the additional base pairs disclosed in FIG. 2 be incorporated enzymatically into DNA and RNA, they could be useful for a variety of purposes. For example, RNA molecules prepared by transcription, although it is known to be a catalyst under special circumstances (a) Cech, T. R.; Bass, B. L. *Ann. Rev. Biochem.* 1986, 55, 599. (b) Szostak, J. W. *Nature* 1986, 332, 83. (c) Been, M. D.; Cech, T. R. *Science* 1988, 239, 1412), appear to have a much smaller catalytic potential then proteins because they lack building blocks bearing functional groups. Conversely, the limited functionality present on natural oligonucleotides constrains the chemist attempting to design catalytically active RNA molecules, in particular, RNA molecules that catalyze the template-directed polymerization of RNA.

Additional base pairs could relax these constraints, especially if their hydrogen bonding pattern differed from those in the AT and GC base pairs, as novel hydrogen bonding schemes would allow additional base pairs to be incorporated enzymatically at specific positions in an oligonucleotide molecule (Switzer, C. Y, Moroney, S. E. & Benner, S. A. *J. Am. Chem. Soc.*, 1989, 111, 8322). If functionalized, such additional bases should also allow the incorporation by transcription of functional groups directly into RNA; the remaining unfunctionalized building blocks could then control secondary structure without introducing over-functionalization and attendant non-specific catalysis. Further, bases bearing functional groups at the position structurally analogous to the 5-position of the uridine ring should be substrates for most polymerases (Leary, J. L., Brigati, D. J. & Ward, D. C. *Proc. Natl. Acad. Sci.* 1983, 80, 4045). New base pairs should also find use in studies of the structure of biologically important RNA and DNA molecules (Chem, T. R., Churchill, M. E. A. Tullius, T. D. Kallenbach, N. R., Seemann, N. C. (1988) *Biochem.*, 27, 6032) and protein-nucleic acid interactions. Several types of catalytic RNA molecules containing natural bases have been proposed as anti-viral agents, for use in agriculture, and in other areas. (Haseloff, J., Gerlach, W. L. *Nature*, 1988, 334, 585; Sarver, N., Cantin, E. M., Chang, P. S., Zaia, J. A., Ladne, P. A., Stephens, D. A., Rossi, J. J. *Science*, 1990, 247 1222–1225). Catalytic RNA molecules incorporating additional bases should be even more useful in certain of these applications. A segment of DNA or RNA containing the additional bases could be replicated only in the presence of triphosphates of the complementary additional bases, allowing the selective copying of DNA containing the additional bases in the presence of DNA containing normal bases, and vice versa. More speculatively, the extra letters in the nucleoside alphabet might eventually be used to expand the genetic code, increasing the number of amino acids that can be incorporated translationally into proteins Noren, C. J., Anthony-Cahill, S. J., Griffith, M. C. & Schultz, P. G. *Science*, 1989, 244, 182; J. D. Bain, J. C. G. Glabe, T. A. Dix, A. R. Chamberlain *J. Am. Chem. Soc.* 1989, 111, 8013–8014.

The process disclosed here involves the incubation of an oligonucleotide template containing one or more non-standard bases with either a DNA or RNA polymerase (Uhlenback, O. C. *Nature*, 1987, 328, 18) in the presence of triphosphates of the complementary nucleosides.

Experiments with iso-C and iso-G (FIG. 2) have shown that bases with novel hydrogen bonding schemes can be incorporated by DNA and RNA polymerases. Thus, this base pair fulfills the criteria outlined above. However, certain forms of iso-C were found to hydrolyze slowly to U under conditions of DNA synthesis, introducing into a template a base that pairs with A in the place of a base that pairs with iso-G. Further, iso-G exists to some extent in a minor tautomeric form that is complementary to U and T. Although the existence of a minor tautomeric form of iso-G has some advantages in certain circumstances (e.g., when one wishes to introduce iso-G into an oligonucleotide duplex opposite U or T), these problems complicate the selective incorporation of the iso-C/iso-G base pair in oligonucleotides also containing A and T. Therefore, the search for a preferred embodiment was directed towards base pairs in FIG. 2 where the non-standard base is joined to the sugar by a carbon-carbon bond, where chemical considerations suggested that hydrolysis and tautomeric equilibria might be less problematic.

Much work was directed towards the pyridine nucleoside analog, 3-$\beta$-D-ribofuranosyl-(2,6-diaminopyridine). However, the presently preferred base pairs are those where the six-ring pyrimidine analog is joined to a ribose or deoxyribose ring via a carbon-carbon bond, and where the pyrimidine analog contains at least two nitrogens in the ring itself. Give an appropriate arrangements of hydrogen bond donating and accepting groups, many ring systems are appropriate (FIG. 4), including ring systems to which are appended functionalized and unfunctionalized side chains. Syntheses for many of these compounds are known in the prior art. (Bartolomew, D. G., Dea, P., Robins, R. K. Revenkar, G. R. (1975) *Org. Chem.*, 40, 3708). However, there are several constraints on the ring system and its substituents. First, the ring systems must be aromatic so that they are capable of stacking with base above and below in the double helix. Second, substituent on the 6 position of the pyrimidine (or the analogous position of a pyrimidine analog) and the 8 position of the purine (or the analogous position of a purine analog) is preferably no larger than hydrogen.

The most preferred pyrimidine analog is 3-$\beta$-D-ribofuranosyl-(2,6-diaminopyrimidine), trivially designated here as K. Several complementary purines are presently preferred. For example, either xanthosine or 3$\beta$-D-ribofuranosyl-(1-methyl-pyrazolo[4,3-d]pyrimidine-5,7(4H,6H)-dione), also known as 7-methyl oxoformycin B, have been found to form base pairs with K when incorporated into DNA and RNA.

EXAMPLE 1

The K-P Base Pair

The pyrimidine 3$\beta$-D-ribofuranosyl-(2,6-diaminopyrimidine), trivially designated as K, presents a donor-acceptor-donor hydrogen bonding pattern to a complementary strand in a duplex structure. K as a deoxyriboside derivative suitable for automated DNA synthesis was synthesized from a known precursor by routes known in the prior art. C. K. Chu, U. Reichman, K. A. Watanable, J. J. Fox, *J. Org. Chem.* 1977, 42, 711. Two purine analogs were chosen to complement K. The first, xanthosine (X), is a natural base available commercially as both the nucleoside and nucleoside triphosphate. However, because of concerns that deoxyxanthosine might undergo depurination in some of the studies planned, another complementary base, 3-$\beta$-D-ribofuranosyl-(1-methyl-pyrazolo[4,3-d]pyrimidine-5,7(4H,6H)-dione) (B. G. Ugarkar, G. R. Revankar, R. K. Robins, *J. Heterocycl. Chem.*, 21, 1965–1870 (1984)), also known as 7-methyl oxoformycin B, and trivially designated here as P, was prepared by routes known in the prior art. In P, the heterocyclic base is joined to the pentose ring by a carbon-carbon bond.

The K-P base pair has physical and chemical properties suitable as replicatable components of a genetic alphabet (J. A. Piccirilli, T. Krauch, S. E. Moroney, S. A. Benner, *Nature*, 343, 33–37 (1990). In a solution of a derivative of K in chloroform, a strong nuclear Overhauser enhancement (NOE) between the proton at C1' of the ribose ring and the proton at C4 of the heterocyclic ring suggested that K adopts the undesired syn conformation when alone in solution. However upon addition of a protected derivative of the complementary purine nucleoside P, this NOE largely disappeared. Further, when both K and its complement are present, the resonances assigned to the amine protons of K shift strongly downfield, as does the resonance of P assigned to the nitrogen flanked by the carbonyl groups. These facts together show that K and P form a standard Watson-Crick base pair in a solution of chloroform.

To determine the effect of a base pair between K and P on the stability of a DNA duplex, several oligonucleotides containing the K-P base pair were synthesized using an Applied Biosystems Oligonucleotide Synthesizer. Melting studies showed that duplexes containing a K-P base pair are only slightly less stable than duplexes containing only natural bases. Further, duplexes containing the new base pair are considerably more stable than those containing mismatches involving the new bases, which in turn had melting temperatures similar to duplexes containing mismatches of natural bases (Piccirilli et al., op. cit.). The stability of various mismatches was consistent with the presumed stability of "wobble" base pairs, which should be particularly important for the GT and AK mismatches. These results suggested that enzymatic incorporation of a new base selectively opposite its complement in a DNA template should be possible, provided that natural DNA and RNA polymerases accepted the new bases.

To demonstrate that xanthosine triphosphate could be incorporated enzymatically into an RNA oligonucleotide opposite a K in the template, a promoter-template including a promoter sequence of T7 RNA polymerase (Milligan, J. F., Groebe, D. R., Witherell, G. W., & Uhlenbeck, O. C. *Nucleic Acids Res.*, 15, 8783 (1987), (17 bases) followed by a short olignucleotide segment (7 bases), the new base K, 1 additional base, and a final A was synthesized, together with a complementary 18 base primer (FIG. 5). Incorporation of K into the synthetic DNA templates was verified by digestion of samples of the template with snake venom phosphodiesterase, hydrolysis of the phosphate from the products with bacterial alkaline phosphatase, and analysis of the resulting nucleosides by HPLC (data not shown). Control templates containing T replacing K were also prepared by synthesis. Transcription of the primed templates could be detected most simply by the incorporation of radiolabled UMP (from a-labeled UTP) into a product RNA molecule 10 bases long (the "full length product").

When synthetic template 1 was incubated with labeled UTP and various other nucleoside triphosphates, full length products were observed in the presence of XTP. The efficiency of synthesis of full length product from templates with and without K was approximately the same, provided that the necessary complementary nucleoside triphosphates were all present in the incubation mixtures. In absence of XTP, a significant amount of full length product could be detected only in the presence of ATP, and this at somewhat low levels (ca. 24%, measured by scintillation counting of bands cut from the gel). Such a misincorporation presumably occurs via "wobble" base pairing, and is not infrequent even with natural bases when incorporation experiments are run in incubation mixtures that are missing one component. Coleman, J. E., Martin, C. T. & Muller, D. K. *Biochemistry*, 27, 3966 (1988).

To determine whether misincorporation of A was diminished by competition with X, experiments were performed with tritiated XTP (synthesized from tritiated GTP by Demijanov oxidation) Roy, K. B. & Miles, H. T. *Nucleosides and Nucleotides*, 2, 237 (1983) and $\gamma$-$^{32}$P-labeled GTP (which is incorporated, with the triphosphate intact, at the 5' end of the RNA product) together in an incubation mixture in varying ratios. Full length products from an incubation containing a 1:1 molar ratio of $^3$H-XTP and unlabeled ATP were isolated by gel electrophoresis, the bands excised, and the relative amounts of $^3$H and $^{32}$P determined by scintillation counting. After correction for the specific activities of the starting nucleotides, the misincorporation of adenosine into the product at a XTP:ATP ratio of 1:1 was reduced to ca. 14%. Infidelity further decreases with increasing ratios of X:A, and most likely stems from errors made by the polymerase itself rather than from minor tautomers of the bases.

To demonstrate that xanthosine triphosphate could be incorporated into a DNA oligonucleotide opposite a K in the template, a set of primer-templates (FIG. 5) were prepared containing either K, C or T (the latter two serving as control templates). Incorporation of K into the synthetic DNA templates was again verified by digestion of samples of the template with snake venom phosphodiesterase, removal of the phosphate from the products by bacterial alkaline phosphatase, and analysis of the resulting nucleosides by HPLC. As before, the last base in the template was a unique A, permitting the detection of full length products most simply by autoradiography following the incorporation of $\alpha$-$^{32}$P-TTP.

The synthetic primer-templates were incubated with the Klenow fragment of DNA polymerase I (Pol 1) Cobianchi, F. & Wilson, S. H. *Meth. Enzymol.*, 152, 94 (1987) in the presence of various nucleoside triphosphates, and the products analyzed by gel electrophoresis. K in the template directed the incorporation of XTP into full length product. Upon electrophoresis, the product containing X migrates faster than the analogous products containing G or A, presumably because the xanthine heterocycle carries an additional negative charge under the conditions of the electrophoresis due to its low $pK_a$ ($pK_a = 5.7$). Direct evidence for the incorporation of xanthosine was obtained by digestion of the product oligonucleotide, kinasing, and electrophoretic analysis.

To measure the relative efficiency as templates of the oligonucleotides containing different bases, product bands from electrophoresis gels were excised and their radioactivity determined by liquid scintillation counting. Templates containing K were ca. 70% as efficient at directing the synthesis of full length product (in the presence of XTP) as those containing only natural bases.

The fidelity of incorporation of X opposite K was examined by incubating templates containing C, T and K with purine triphosphates separately and in competition (FIG. 5). As expected, the fidelity of incorporation was considerably higher with DNA polymerase than with T7 RNA polymerase. Essentially no G or A was incorporated by the Klenow fragment of DNA polymerase opposite K, and essentially no X was incorporated opposite T in the template. The only evidence of infidelity was a low level (ca. 5%) of X misincorporated opposite C in the template when GTP was missing from the incubation mixture. This misincorporation was not observed at all when GTP and XTP were present in a 1:1 ratio.

EXAMPLE 2

The isoC-isoG Base Pair

Protected d-iso-C suitable as a building block for the chemical synthesis of DNA was synthesized by direct extensions of standard methods. Watanabe, K. A.; Reichman, C. K.; Fox, J. J. *Nucleic Acid Chemistry;* Tipson, R. S.; Townsend, L. B., Eds.; John Wiley and Sons: New York 1978; Part 1, p 273. (b) Kimura, J.; Yagi, K.; Suzuki, H.; Mitsunobu, O. *Bull. Soc. Chem. Jap.* 1980, 53, 3670. N$^2$-benzoyl-5'-dimethoxytrityl-d-iso-C diisopropyl phosphoramidite, used directly in machine-DNA synthesis, was synthesisized from d-iso-C by the general procedure of Atkinson and Smith: Atkinson, T.; Smith, M. *Oligonucleotide Synthesis: A Practical Approach;* Gait, M. J. Ed.; IRL Press: Oxford 1985; pp 35–82. This was incorporated into two templates, and three other templates containing only natural bases were synthesized for use as standards and controls. An 8-mer primer was annealed to the appropriate templates (FIG. 5) to provide a double stranded binding site for the Klenow fragment of DNA polymerase I (*E. coli*), followed by a single stranded coding region containing d-iso-C flanked only by purine nucleotides. Alternatively, different templates (FIG. 5) were annealed to an 18-mer to give the double stranded promoter region required by T7 RNA polymerase, followed by a single stranded coding region containing d-iso-C. In all of the templates, a unique A at the end of the coding strand was included to direct the incorporation of radiolabelled T or U and ribo- and deoxyribo-iso-GTP's. Mantsch, H. H. et. al., *Biochemistry* 1975, 14, 5593. The reactions with the Klenow fragment were conducted by incubating template/primer, polymerase, and a mixture of the required dNTPs including ($\alpha$-$^{32}$P)TTP. Following incubation, the products were analyzed by gel electrophoresis and autoradiography. With primed templates containing iso-C, full length product was obtained only with d-iso-GTP present in the incubation mixture. The presence of iso-G at the correct position in the product oligonucleotide was positively established by a "nearest neighbor" analysis, Sgaramella, V.; Khorana, H. G. *J. Mol. Biol.* 1972, 72, 427. and by the "minus" sequencing method. Sanger, F.; Coulson, A. R. *J. Mol. Biol.* 1975, 94, 441. As expected, in an incubation of a primed template containing T with dATP and the required dNTPs in the absence of d-iso-GTP, full length product was observed only to the extent anticipated by the fact that a small amount (15%) of dUTP was present in the template due to the deamination of iso-C (vide supra).

Infidelity between iso-G and T was anticipated due to the known existence of a minor "phenolic" tautomer of iso-G in addition to the major $N_1$-H tautomer (Sepiol, J., Kazimierczuk, Z., Shugar, D. Z. *Naturforsch.*, 1976, 31c, 361; the possibility that this minor tautomer could form a Watson-Crick base pair with T was recognized on theoretical grounds. In fact, incubation of a primed template containing T in place of d-iso-C with the required dNTPs and d-iso-GTP did yield a significant amount of full length product. This result strongly suggests that polymerases synthesize a base pair between T and the "phenolic" tautomer of iso-G. This fact diminishes the value of the base pair between iso-G and iso-C for many (but not all applications.

In analogous experiments, T7 RNA polymerase was shown to accept the new base pair. Incubation of a template (FIG. 5) possessing the T7 promoter with the required NTPs yielded more full length product in the presence iso-GTP than in its absence. Sequencing of the RNA transcript positively established the presence of iso-G in the product at the expected position.

---

What is claimed is:

1. A method for incorporating into a DNA or RNA oligonucleotide chain at least one nucleotide unit bearing a heterocyclic base selected from the group consisting of the structural formulae of FIG. 4, wherein —R designates the point of attachment of the base to position 1 of a ribose or deoxyribose ring, X is either a nitrogen atom or a carbon atom bearing a substituent Z, Z is either a hydrogen, an unfunctionalized lower alkyl chain, or a lower alkyl chain bearing an amino, carboxyl, hydroxyl, thiol, aryl, indole, or imidazolyl group, Y is either N or CH, and each ring contains no more than three nitrogens consecutively bonded, that consists of synthesizing a template that is an oligonucleotide containing one or more nucleotide subunits bearing a heterocyclic base selected from the group consisting of the structural formulae of FIG. 4, dissolving this template in buffered aqueous solution, adding to the solution nucleoside triphosphates complementary to the nucleotide subunits in the template, adding to this solution a solution of a DNA or RNA polymerase, and incubating said mixture of the solutions such that an oligonucleotide chain complementary to the template and incorporating said at least one oligonucleotide unit bearing a heterocyclic base selected from the group consisting of the structural formulae of FIG. 4 is synthesized.

2. The method of claim 1 wherein said heterocyclic base is selected from the group consisting of 2,6-diaminopyrimidine, xanthine, 2,6-diaminopyrazine, 1-methyl-pyrazolo[4,3-d]pyrimidine-5,7(4H,6H)-dione, iso-guanine, and iso-cytosine.

3. The method of claim 1 wherein said polymerase is selected from the group consisting of the Klenow fragment of DNA polymerase I, T7 RNA polymerase, and AMV reverse transcriptase.

4. The method of claim 1 wherein said heterocyclic base is iso-cytosine incorporated opposite iso-guanine in a template.

5. The method of claim 1 wherein said heterocyclic base is iso-guanine incorporated opposite iso-cytosine in a template.

6. The method of claim 1 wherein said heterocyclic base is 2,6-diaminopyrimidine or 2,6-diaminopyrazine incorporated opposite 1-methyl-pyrazolo[4,3-d]pyrimidine-5,7(4H,6H)-dione or xanthine in a template.

7. The method of claim 1 wherein said heterocyclic base is 1-methyl-pyrazolo[4,3-d]pyrimidine-5,7(4H,6H)-dione or xanthine incorporated opposite either 2,6-diaminopyrimidine or 2,6-diaminopyrazine in a template.

* * * * *